United States Patent [19]

Cohn et al.

[11] Patent Number: 4,826,945

[45] Date of Patent: May 2, 1989

[54] BIODEGRADABLE POLYMERIC MATERIALS BASED ON POLYETHER GLYCOLS, PROCESSES FOR THE PREPARATION THEREOF AND SURGICAL ARTICLES MADE THEREFROM

[75] Inventors: Daniel Cohn, Jerusalem; Hani Younes, Ara-Meshulush; Gideon Uretzky, Jerusalem, all of Israel

[73] Assignee: Yissum Research Development Company, Jerusalem, Israel

[21] Appl. No.: 201,403

[22] Filed: Jun. 2, 1988

[30] Foreign Application Priority Data

Jun. 9, 1987 [IL] Israel ......................................... 82834

[51] Int. Cl.[4] ............................................. C08G 18/34
[52] U.S. Cl. ......................................... 528/76; 424/78; 428/423.7; 428/480; 525/450; 604/19
[58] Field of Search .................. 528/76, 271; 525/450; 428/423.7, 480; 424/78; 604/19

[56] References Cited

U.S. PATENT DOCUMENTS 4,355,133 10/1982 East et al. ............................ 528/271

*Primary Examiner*—Maurice J. Welsh
*Attorney, Agent, or Firm*—Cushman, Darby & Cushman

[57] ABSTRACT

The invention provides poly($\alpha$-hydroxy-carboxylic acid)/poly(oxyalkylene) polymers selected from multiblock polymers of the following repeating unit I

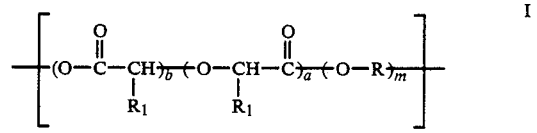

wherein R is an alkylene group, $R_1$ is hydrogen or methyl groups, m is a positive integer, and a and b are zero or positive integers, the case where a and b are simultaneously zero being excluded, and chain extended multiblock polymers which polymers are bioabsorbable and biodegradable, these polymeric materials being derived from reacting diols in the form of polyether glycols with $\alpha$-hydroxy-carboxylic acids. The invention also provides methods for the preparation of such polymeric materials and bioabsorbable surgical articles made therefrom.

43 Claims, No Drawings

BIODEGRADABLE POLYMERIC MATERIALS BASED ON POLYETHER GLYCOLS, PROCESSES FOR THE PREPARATION THEREOF AND SURGICAL ARTICLES MADE THEREFROM

The present invention relates to new and useful bioabsorbable polymeric materials derived from reacting diols in the form of polyether glycols with α-hydroxycarboxylic acids, to methods for the preparation of such polymeric materials and products such as surgical articles derived therefrom.

The development of bioabsorbable polymers is an important area in the biomedical materials field. The most obvious advantage is that it eliminates the need of reoperation for prostheses removal following use. Such polymers can perform as a temporary scaffold for tissue regeneration, as a transient barrier or in controlled drug release systems.

The most indispensable attribute of a biodegradable material relates to the biocompatibility of both the polymer at implantation time and the products of its degradation process. Additional parameters which play an important role include the mechanical properties of the material and, for most applications, the matching of the polymer biodegradation kinetics to that of the healing process.

The scarcity of polymers which meet these rather demanding requirements has prompted a continuous search for new, improved biodegradable polymers.

Polyglycolic acid (PGA) was the first biodegradable polymer synthesized and is used mainly to prepare bioabsorbable sutures (E. E. Schmitt and R. A. Polistina, U.S. Pat. No. 3,297,033 (1967); E. J. Frazza and E. E. Schmitt, J. Biomed. Mater. Res., 1 43–58 (1971); it was followed by polylactic acid (PLA) and copolymers of the two (A. K. Schneider, (Du Pont), U.S. Pat. No. 2,703,316. A. K. Schneider, U.S. Pat. No. 3,636,956 (1975); R. K. Kulkarni, K. C. Pani, C. Neuman and F. Leonard, J. Biomed. Mater. Res., 5, 169 (1971); D. Wasserman, U.S. Pat. No. 1,375,008 (1971); D. K. Gilding and A. M. Reed, Polymer, 20, 1459–1464 (1979); A. M. Reed and D. K. Gilding, Polymer, 22, 494–498 (1981)). These alpha polyesters have been investigated for use as sutures and as implant materials for the repair of a variety of osseous and soft tissues (J. O. Hollinger, J. Biomed Mater. Res., 17 71–82 (1983); D. E. Cutright and E. E. Hunsuck, Oral Surg., 33 28–34 (1972); L. Audell, S. Bowald, C. Busch and I. Eriksson, Acta Chir. Scand. 146, 97–99 (1980), as well as in sustained drug delivery applicatons (T. M. Jakanicz, H. A. Nash, D. L. Wise and J. B. Gregory Contraception, 8, 227 (1973); L. R. Beck, D. R. Cowsar, D. H. Lewis, R. J. Coxgrove, C. T. Riddle, S. L. Lowry and T. Epperly, Fert. Ster. 31, 545 (1979)).

However, due to some characteristics of these α-hydroxy-carboxylic acids, more importantly their slow degradation kinetics and their stiffness, it has long been recognized that a need exists for new absorbable polymers, exhibiting the advantageous properties of strength, flexibility and absorbability needed for various biomedical applications.

There have been various prior art suggestions for modifying polyglycolic and polylactic acid, such as by copolymerization of glycolide or lactide monomers with other monomers, to produce a polymer possessing the requisite properties. For example, the work by C. X. Song and X. D. Feng, who developed a series of ABA triblock copolymers of ε-caprolactone and DL-Lactide macromolecules, 17, 2764 (1984)), or the development of polyesteramides, by T. H. Barrows (U.S. Pat. No. 4,343,931). Other copolymers for use as bioabsorbable materials have been disclosed. Polyethylene oxide/polyethylene terephthalate copolymers have been disclosed as biodegradable elastomeric biomaterials in Reed et al., "Trans. Am. Soc. Artif. Intern. Organs", 1977, page 109. U.S. Pat. No. 2,917,410 discloses the condensation of glycolic acid with a polyethylene glycol mixture to an ester with an average molecular weight of 5105 for treating fabrics for improved tear strength and abrasion resistance. The addition of aromatic orthocarbonates during the formation of a fiber-forming polyester by the reaction of a dicarboxylic acid or its functional derivative with a glycol is disclosed in U.S. Pat. No. 3,714,125.

U.S. Pat. No. 4,070,347 discloses poly (orthoester) co- and homopolymers and poly(orthocarbonate) co- and homopolymers useful for forming delivery devices with drug dispersed therein for release by controlled polymeric erosion over a prolonged period of time. U.S. Pat. No. 4,343,931 discloses poly(esteramides), which are condensation products of reacting a diamine with lactic or glycolic acid to form a diaminediol which is then reacted with a bischloroformate or a dicarboxylic acid. Important biodegradable polymers developed in recent years include a new class of bioerodible polyanhydrides, developed by Langer, especially for controlled drug delivery (H. B. Rosen, J. Chang, G. E. Wnek, R. J. Linhardt and R. Langer, Biomaterials, 4,131(1983); K. W. Leong, B. C. Brott and R. Langer, J. Biomed. Mater. Res., 19 (8), 941 (1985).

Among the requirements of an ideal absorbable polymeric material are that it should have adequate strength and flexibility, should be controllably uniform in properties, should be absorbable by living tissue, preferably at a constant rate regardless of the place of the body or the condition of the patient, without causing unfavorable tissue reactions as walling off, granuloma formation, excessive edema, etc., it should cause minimal thrombosis in blood-contacting applications, it should have good handling properties, and finally it should be sterilizable without significantly affecting desired properties of the material. Additional requirements are dictated by its specific appliation. For example, the acceptability of a suture is frequently determined by the Young modulus (a measurement of flexibility), the tensile strength and the percent elongation at the breaking point (a measure of extensibility).

According to the present invention there is now provided synthetic absorbable polymers having a high degree of softness and flexibility, while covering a wide range of biodegradation kinetics. Thus the present invention provides synthetic absorbable polymers having unique and desirable properties not available with the biodegradable polymers of the prior art.

More specifically, the present invention provides copolymers from which can be manufactured absorbable surgical articles such as sutures, wound and burn dressings and partially or totally biodegradable vascular grafts, possessing the desired characteristics of flexibility, strength, biocompatibility, biodegradability and sterilizability. Such is achieved, according to the invention, through the copolymerization of lactic or glycolic acid or combinations of the two, with hydroxy-ended flexible chains, most preferably poly(alkylene glycols) of various molecular weights, to produce absorbable copolymers possessing increased flexibility and covering a wide range of biodegradation rates.

Thus according to the present invention there are now provided poly(α-hydroxy-carboxylic acid)-/poly(oxyalkylene)s selected from:

(a) multiblock polymers of the following repeating unit I

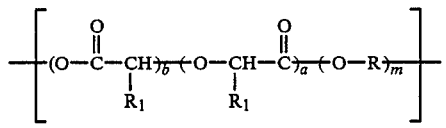

wherein R is an alkylene group, $R_1$ is hydrogen or methyl groups, m is a positive integer, and a and b are zero or positive integers, the case where a and b are simultaneously zero being excluded, and (b) a chain extended multiblock polymer of the following formula II:

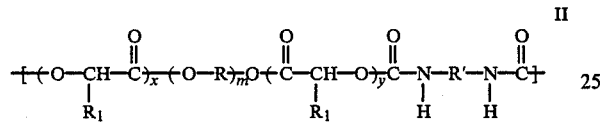

wherein R represents an alkylene group, $R_1$ is hydrogen or methyl groups and R' is hexamethylene, 4,4'-diphenylmethane, toluene, naphtalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene and p-phenylene, or diisocyanate-terminated polyalkylene glycol chains comprising a central polyalkylene glycol chain capped by two diisocyanate compounds of the above, or (c) a chain extended multiblock polymer of the following formula III

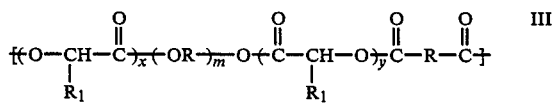

wherein R represents an alkylene group, $R_1$ is hydrogen or methyl groups, R" is a saturated or unsaturated alkylene group, or an aromatic ring, x and y are identical or different positive integers, and m is a positive integer.

The copolymers of this invention are multiblock copolymers obtained through the polyesterfication of the α-hydroxycarboxylic acid in the presence of hydroxyl-ended poly(alkylene glycol) chains of various molecular weights. The degree of polymerization of the copolymer was varied depending on various experimental parameters. Most noticeably temperature, pressure and time. A preferred poly(alkylene glycol) is poly(ethylene glycol), preferably in the 600–6000 molecular weight range.

The invention also provides a method of polymerization for producing said poly(α-hydroxy-carboxylic acid)/poly(alkylene glycol) block copolymers.

As indicated hereinbefore the polymers of the invention find advantageous utility in the manufacture of surgical articles and pharmaceutical compositions as is known in the art for polymers, absorbable in living animals. Thus, the present invention also provides surgical articles including a suture or ligature, particularly in the form of flexible monofilaments, a suture in the form of a needle and a suture combination, a surgical clip or staple, a surgical prosthesis, a partially or totally biodegradable vascular graft, wound and burn covering, textile structures, couplings, tubes, supports, pins, screws or other forms of support. Yet further objects of this invention include a self-supporting film, hollow tube, beads or gel, containing a uniformly dispersed drug for controlled continuous administration, manufactured from polymers of the present invention.

Thus the invention also provides surgical articles comprised of:

(1) a multiblock polymer of the following repeating unit:

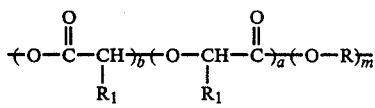

wherein R is an alkylene group, $R_1$ is hydrogen or methyl groups, m is a positive integer, and a and b are zero or positive integers, the case where a and b are simultaneously zero being excluded.

The copolymers of this invention are obtained by the polycondensation reaction of monomeric α-hydroxycarboxylic acids, having the formula

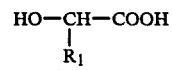

wherein $R_1$ is hydrogen or methyl groups, in the presence of hydroxyl-ended poly(alkylene glycol) chains having the general formula H—(OR—)$_m$—OH wherein R is an alkylene group such as ethylene, propylene, butylene or combinations of them, in the presence of an esterfication promoting catalyst such as $Sb_2O_3$, to produce the copolymer.

Additional dihydroxy compounds that can be used include the already mentioned poly(alkylene glycols) and also ethylene glycol; 1,3-propanediol; 1,4-butanediol; 1,5-pentanediol; 1,6-hexanediol; 1,7-heptanediol; 1,8-octanediol; 1,9-nonanediol; 1,10-decanediol; 1,11-undecanediol; 1,12-dodecanediol; 1,13-tridecanediol; 1,14-tetradecanediol; 1,15-pentadecanediol; 1,16-hexadecanediol; oxaaliphatic diols, diaminediols, hydroxy-terminated polydimethyl siloxane polymers and copolymers, and poly(butadiene, hydroxyl terminated).

A particularly preferred poly(alkylene glycol) is polyethylene glycol (other commonly used names are poly(oxyethylene) and polyethylene oxide); therefore, the following description and first examples, which are presented by way of illustration, are directed primarily to the synthesis of copolymers comprising polyethylene glycol chains, it being understood that certain variations may apply to other poly(alkylene glycols) encompassed by the general formula of the invention (described in less detail in later examples) as will be readily apparent to those skilled in the art.

PELA is the generic name used to denote this family of polyethylene glycol (PEG) and lactic acid (LA) copoly (ether-esters). The average molecular weight of the PEG chains is listed after the name, this being followed by $\bar{x}$, the segmental degree of polymerization of the LA sequences (e.g., PELA3400/209).

The one-step synthesis of the multiblock copolymer is exemplified as follows, for a poly(ethylene glycol)-/polylactic acid, PELA copolymer.

During this first stage of the reaction, an ABA triblock polymer is formed, its overall molecular weight and the length of the different segments being determined by the molecular weight of the polyalkylene glycol chain, by the feed of lactic acid into the system and by reaction time. Raising the temperature of the system was expected, as it would be readily apparent to those skilled in the art, to increase the reaction rate. Surprisingly, however, raising the temperature caused a drastic change in the reaction mechanism, a completely unexpected and rather unusual pathway being now available for further increase of the molecular weight. Most probably an ester alkyl-oxygen scission mechanism of lactoyl units is responsible for the large increase in molecular weight and the consequent dramatic changes in the polymers' properties. The second stage of the reaction yields a polymer of the following general repeating unit:

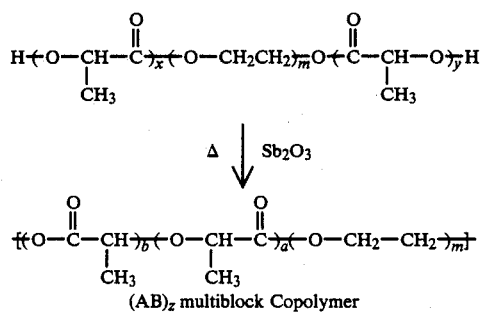

(AB)$_z$ multiblock Copolymer wherein m is a positive integer, and a and b are zero or positive integers, provided a and b are not simultaneously zero.

U.S. Pat. No. 4,452,973 discloses poly(glycolic acid)-/poly(oxyethylene) triblock copolymers and method of manufacturing the same, while U.S. Pat. No. 4,438,253 describes a poly(glycolic acid)/poly (alkylene glycol) block copolymer and the method of manufacturing the same. These multiblock copolymers are synthesized via a three-steps process, whereby triblock copolymers comprising a poly(alkylene glycol) chain and two poly(glycolic acid) (PGA) blocks are chain extended by an aromatic orthocarbonate such as tetra-p-tolyl orthocarbonate. The substantial stiffness of the copolymers prepared according with the teachings of this reference (a 2.75 GPa modulus is presented in Example 6 of U.S. Pat. No. 4,438,253 as illustrating the greater flexibility of the materials developed), makes these materials unsuitable for use as flexible surgical articles and conclusively precludes their use in a variety of biomedical applications. The large PGA content (80–85%) readily explains the rigidity of the materials obtained, their stiffness being comparable to that of, for example, polymethyl methacrylate, twice that of polypropylene and approximately twenty-five times that of silicone rubber. The high PGA content is also responsible for the high melting point of these crystalline materials (Tm=217°–220°) and can be assumed, will also result in severely limited solubility properties. It is also important noticing the extremely narrow compositional range covered by the polymers disclosed by the invention (80–85% PGA), resulting, therefore, in a strikingly limited range of biodegradation processes, the materials developed following an essentially similar degradation kinetics. It should also be stressed, that the process comprises the transesterification reaction of PGA and hydroxy-terminated poly(alkylene glycol) chains (U.S. Pat. No. 4,438,253, claim 7), the polymerization of monomeric GA to produce PGA, being a previous and separate reaction. Finally, the addition of an aromatic orthocarbonate chain extender is a third step, required to increase the molecular weight of the polymer and reduce its brittleness.

Clearly contrasting with this description of the invention disclosed in U.S. Pat. No. 4,438,253, it is readily apparent that the rather special chemistry involved in the fundamental stage of the process of the present invention, plays a crucial role in allowing a very simple one-step full polymerization process, and resulted in a variety of polymeric materials exhibiting very special mechanical features (most importantly, their extremely high flexibility, attaining E=5 MPa and $\epsilon_F$=1100% values, in some instances) and covering a wide range of degradation kinetics. In light of these findings, it is apparent that the present invention provides synthetic absorbable polymers having unique and desirable properties not available with the biodegradable polymers of the prior art, and that the method presented hereby is markedly more advantageous than that of the prior art.

Alternatively, the degree of polymerization of the ABA Copolymer is increased by (a) reacting various di-isocyanates such as hexamethylene diisocyanate (HDI), 4,4'-diphenylmethane diisocyanate (MDI), 4,4'-dicyclohexylmethane diisocyanate (H$_{12}$MDI), cyclohexyl diisocyanate (CHDI) and 2,4 toluene diisocyanate (TDI), of the following formula:

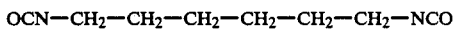

HDI

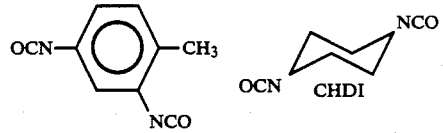

TDI    CHDI

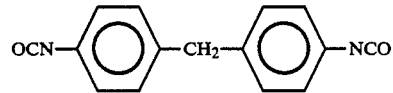

MDI

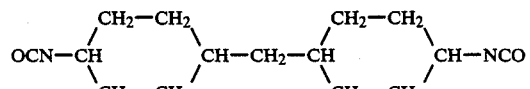

H$_{12}$MDI with the terminal hydroxyl groups of the ABA type polymer.

The reaction yielded a series of poly(etherester urethanes). The reaction is carried out in dry solvents such as tetrahydrofuran or dimethylformamide or in the melt, in presence of an appropriate urethanization promoting catalyst such as dibutyltin dilaurate. The chain extension step is exemplified as follows for a polyethylene glycol containing copolymer:

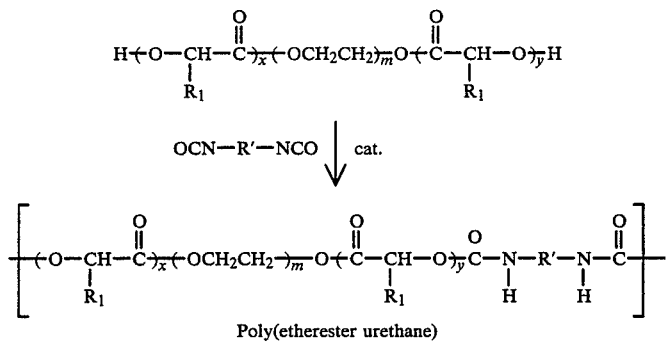

Poly(etherester urethane)

Poly(etherester urethane)
wherein $R_1$ represents hydrogen or methyl groups and R' may be hexamethylene, 4,4'-diphenylmethane, toluene, napthalene, 4,4'-dicyclohexylmethane, cyclohexyl, 3,3'-dimethylphenyl, 3,3'-dimethyl-diphenylmethane, 4,6' xylene, 3,5,5-trimethylcyclohexyl, 2,2,4-trimethylhexamethylene and p-phenylene, or diisocyanate terminated polyalkylene glycol chains comprising a central Polyalkylene chain, capped by two diisocyanate compounds of the above, and (b) reacting a compound selected from the group consisting of dicarboxylic acids, methyl and ethyl esters of dicarboxylic acids, diacid chlorides and anhydrides of a dicarboxylic acid. Dicarboxylic acids and derivatives useful in the synthesis of polymers by the above methods include those derived from the dicarboxylic acids listed below. In addition the free acids can also be used. They are, for example, oxalic acid, malonic acid; succinic acid; 2,3-dimethylsuccinic acid; glutaric acid; 3,3-dimethylglutaric acid; 3-methyladipic acid; adipic acid; pimelic acid; suberic acid; azelaic acid; sebacic acid; 1,9-nonanedicarboxylic acid; 1,10-decanedicarboxylic acid; 1,11-undecanedicarboxylic acid; 1,12-dodecanedicarboxylic acid; 1,13-tridecanedicarboxylic acid; 1,14-tetradecanedicarboxylic acid; 1,15-pentadecanedicarboxylic acid; 1,16-hexadecanedicarboxylic acid; maleic acid; trans- - hydromuconic acid; fumaric acid; diglycolic acid; 3,3'-oxydipropionic acid; 4,4'-oxydibutyric acid; 5,5'-oxydivaleric acid; 6,6'-oxydicaproic acid; 8,8'-oxydicaprylic acid; 6-oxaundecanedioic acid; 5-oxaazelaic acid; 5- oxasebacic acid; 5-oxaundecanedioic acid; 5-oxadodecanedioic acid; 5-oxatetradecanedioic acid; 5-oxahexadecanedioic acid; 6-oxadodecanedioic acid; 6-oxatridecanedioic acid; 6-oxapentadecanedioic acid; 6-oxaheptadecanedioic acid; 7-oxapentadecanedioic acid; 10-oxanonadecanedioic acid and other oxa-aliphatic dicarboxylic acids; phthalic acid; isophthalic acid; terphthalic acid and other aromatic dicarboxylic acids; 1,2-cyclobutanedicarboxylic acid; 1,4-cyclohexanedicarboxylic acid, poly(butadiene, carboxyl terminated), Poly(oxyalkylene, carboxyl terminated), carboxy-ended polydimethyl siloxane polymers and copolymers.

Polymeric analogs of the above carboxylic acid derivatives containing reactive groups, like esters or anhydrides, can also be used; therefore, polyester or polyanhydrides segments can be successfully incorporated into the copolymeric chain, resulting in higher molecular weights and significantly affecting the properties of the products. The multiblock polymers obtained by carboxylic acids and derivatives have the following formula:

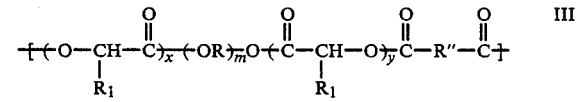

wherein R represents an alkylene group, $R_1$ is hydrogen or methyl groups, R" is an alkylene saturated or unsaturated group or an aromatic ring, according to the carboxylic acid and derivatives listed above, x and y are identical or different positive integers, and m is a positive integer.

The hydroxyl-ended poly(alkylene glycol) useful in the invention may advantageously comprise, among others, hydroxyl-terminated polyethylene oxide, polypropylene oxide, poly(oxyethylene-co-oxypropylene) and polytetramethylene oxide chains. Generally the poly(alkylene)oxides must be water soluble so that they can be excreted by the body once the copolymeric biomaterial has degraded. Examples of poly(alkylene glycols) capable of producing linear polymers are poly(oxyethylene glycols), poly(oxypropylene)-poly(oxyethylene)-glycols block copolymers and poly(oxybutylene) glycols. The foregoing are commercially available in a variety of molecular weights.

Dihydroxy compounds that can be used include the previously mentioned poly(alkylene glycols) and also ethylene glycol; 1,3-propanediol; 1,4-butanediol; 1,5-pentanediol; 1,6-hexanediol; 1,7-heptanediol; 1,8-octanediol; 1,9-nonanediol; 1,10-decanediol; 1,11-undecanediol, 1,12-dodecanediol; 1,13-tridecanediol; 1,14-tetradecanediol; 1,15pentadecanediol; 1,16-hexadecanediol; oxaaliphatic diols, diamine diols, hydroxy-terminated polydimethyl siloxane polymers and copolymers, poly(butadiene, hydroxyl terminated).

The polymeric materials of this invention can be fabricated into films and fibers by melt extension. Such materials have been implanted subcutaneously in mice and have been found to be non-irritating and compatible with the living tissue over the time span of many months. Substantial amounts of the polymer are absorbed by the living tissue, the degration kinetics varying with composition, structure and molecular weight of the polymer.

The polymers of the present invention are also useful in the manufacture of cast and/or extruded films and molded solid surgical aids. Thus, cylindrical pins, screws, reinforcing plates, etc. may be machined from the cast or molded polymer having the aforementioned in vivo absorption characteristics.

The polymers are melt extruded through a spinneret in a conventional manner to form one or more filaments which are subsequently drawn about three to six times in order to achieve molecular orientation and improve tensile properties. The resulting oriented filaments have good tensile and dry knot strength and good in vivo strength retention.

To further improve dimensional stability and tensile strength retention, the oriented filaments may be subjected to an anealing treatment, by heating them at various temperatures for different time periods, while preventing the filaments from measurable shrinking.

The present invention provides synthetic absorbable sutures having a high degree of softness and flexibility while at the same time allowing the sutures to be used in monofilament form. While multifilament sutures manufactured from polymers such as lactide and glycolide fulfill most of the requirements of a suture, monofilament sutures of these materials are considerably less flexible than catgut and these synthetic sutures are accordingly generally limited to a multifilament braided construction. Braided sutures have the disadvantage of causing trauma upon being pulled through tissue due to a sawing action, also known as tissue drag. It is accordingly an object of the present invention to provide synthetic absorbable sutures having unique and desirable properties, as monofilaments or in braided structure, not available with the sutures of the prior art.

Bicomponent filaments composed of two separate materials, at least one of them being one of the polymers of the invention were developed as well.

Fabrics comprising polymeric materials of this invention, alone or in combination with other polymers, have been developed by textile and non-textile techniques. Multicomponent fabrics, woven, knitted, felted, adhesively united or otherwise, comprising at least two different polymers, at least one of them being according to the present invention were prepared. Also fabric tubes having separate strands of bicomponent materials or strands of two separate components, wherein at least one is according to the invention, were produced. A coated fabric, comprising a substantially continuous sheet of a second material or materials was prepared by hot melt coating. A coating from a solvent system or with coating rolls, the base fabric of which may be wholly non-absorbable although it may contain an absorbable component, were produced.

While the invention will now be described in conection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Example 1

Preparation of PELA3400/209 copolymer 17 gr PEG(mw=3400) (0.005 mole) were placed in a 250 ml three-necked flask fitted with a mechanical stirrer and a nitrogen flow inlet, together with 0.12 gram $Sb_2O_3$ and 0.75 gram $H_2PO_4$. The system was flushed with dry nitrogen and heated up to 120° C. 108 grams LA (1.20 mole) were added dropwise during 2 hours, while the temperature was raised gradually to 160° C., and maiantained there for 16 hours. Then the temperature was raised further, to 200° C. for another 16 hours. During all these stages of the polymerization process the reaction vessel was permanently flushed with dry nitrogen. Finally, the temperature was lowered to 135° C., while a 5 mm Hg vacuum was applied to the system, for another 4 hours.

EXAMPLE 2

Preparation of PELA3400/71

The procedure of Example 1 was following using 17 gr PEG (mw=3400) 72 gr LA, 0.08 gr $Sb_2O_3$ and 0.56 gr $H_3PO_4$.

EXAMPLE 3

Preparation of PELA3400/19

The procedure of Example 1 was followed using 17 gr PEG (mw=3400), 54 gr LA, 0.06 gr $Sb_2O_3$ and 0.42 gr $H_3PO_4$.

EXAMPLE 4

Preparation of 6000/277

The procedure of Example 1 was followed using 17 gr PEG (mw=6000), 108 gr LA, 0.12 gr $Sb_2O_3$ and 0.75 gr $H_3PO_4$.

EXAMPLE 5

Preparation of PELA6000/196

The procedure of Example 1 was followed using 17 gr PEG (mw=6000), 90 gr LA, 0.10 gr $Sb_2O_3$ and 0.70 gr $H_3PO_4$.

EXAMPLE 6

Preparation of PELA1500/179

The procedure of Example 1 was followed using 7.5 gr PEG (mw=1500), 90 gr LA, 0.10 gr $Sb_2O_3$ and 0.70 gr $H_3PO_4$.

EXAMPLE 7

Preparation of PELA 1500/45

The procedure of Example 1 was followed using 17 gr PEG (mw=1500), 90 gr LA, 0.10 gr $Sb_2O_3$ and 0.70 gr $H_3PO_4$.

EXAMPLE 8

Preparation of PELA600/24

The procedure of Example 1 was followed using 17 gr PEG (mw=600), 90 gr LA, 0.10 gr $Sb_2O_3$ and 0.70 gr $H_3PO_4$.

EXAMPLE 9

Preparation of PELA600/16

The procedure in Example 1 was followed using 17 gr PEG (mw=.600), 72 gr LA, 0.06 gr $Sb_2O_3$ and 0.56 gr $H_3PO_4$.

EXAMPLE 10

Preparation of PELA3400/141/urethane copolymer

The procedure in Example 1 was followed using 17 gr PEG (mw=3400), 90 gr LA, 0.10 gr $Sb_2O_3$ and 0.70 gr $H_3PO_4$, the last step (135° C. 5 mm Hg) being shortened to 2 hours. The temperature was then lowered to 125° C. and 1.68 gr (0.01 mole) hexamethylene diisocyanate was added; the system was kept at these conditions for 3 hours.

EXAMPLE 11

Preparation of PPLA2000/65 (PPG2000/LA) copolymer

The procedure of Example 1 was followed using 20 gr PPG (polypropylene glycol) (mw=2000), 90 gr LA, 0.10 gr $Sb_2O_3$ and 0.7 gr $H_3PO_4$.

Some properties of the block copolymers produced according to the above examples, compared to those of polyactic acid are set forth in Table I.

TABLE I
Properties of PEO/LA Block Polymers

| Example | MW PEG | wt % PEO by NMR | $Tm_1$(°C.) | $Tm_2$(°C.) |
|---|---|---|---|---|
| 1 | 3400 | 18 | — | 135 |
| 2 | 3400 | 40 | — | — |
| 3 | 3400 | 71 | 44 | — |
| 4 | 6000 | 23 | — | 142 |
| 5 | 6000 | 30 | 44 | 135 |
| 7 | 1500 | 32 | — | 113 |
| 8 | 600 | 26 | — | 105 |
| 10 | 3400 | 25 | — | 120 |
| PLA | — | — | — | 172 |

EXAMPLE 12

Solvent cast films were prepared and standard strips for tensile testing, were prepared. The mechanical analysis of the developed copolymers revealed that, when compared with PLA, they show a substantial decrease in stiffness and a large increase in the elongation at break. Of special interest were highly flexible PELA polymers, exhibiting an elastomeric-like behavior, with a modulus of 5 MPa and elongation at break of 900%.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A poly(α-hydroxy-carboxylic acid)/poly(oxyalkylene) polymer selected from:

(a) a multiblock polymer of the following repeating unit I

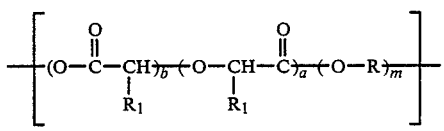

wherein R is an alkylene group, $R_1$ is hydrogen or methyl groups, m is a positive integer, and a and b are zero or positive integers, the case where a and b are simultaneously zero being excluded, or (b) a chain extended multiblock polymer of the following formula II:

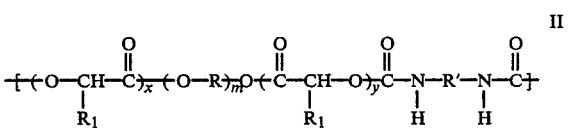

wherein R represents an alkylene group, $R_1$ is hydrogen or methyl groups and R' is hexamethylene, 4,4'-diphenylmethane, toluene, naphtalene, 4,4'-dicyclohexylmethane, cyclohexyl, 3,3'-dimethylphenyl, 3,3'-dimethyl-diphenylmethane, 4,6'-xylene, 3,5,5-trimethylcyclohexyl, 2,2,4-trimethylhexamethylene and p-phenylene, or diisocyanate terminated polyalkylene glycol chains comprising a central polyalkylene glycol chain capPed by two diisocyanate compounds of the above, or (c) a chain extended multiblock polymer of the following formula III

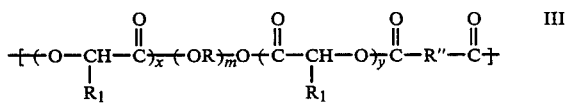

wherein R represents an alkylene group, $R_1$ is hydrogen or methyl groups, R" is a saturated or unsaturated allkylene group, or an aromatic ring, x and y are identical or different positive integers, and m is a positive integer.

2. A multiblock copolymer useful for the manufacture of bioabsorbable surgical articles, having a general repeating unit I

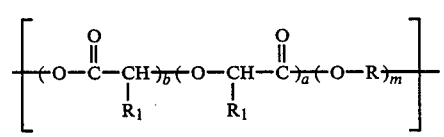

wherein R is an alkylene group, $R_1$ is hydrogen or methyl groups, m is a positive integer, and a and b are zero or positive integers, the case where a and b are simultaneously zero being excluded.

3. A multiblock copolymer as claimed in claim 1 where R is ethylene.

4. A multiblock copolymer as claimed in claim 1 where $R_1$ is hydrogen.

5. A multiblock copolymer as claimed in claim 1 where $R_1$ is methyl.

6. A multiblock copolymer as claimed in claim 1 wherein along the copolymeric chain some $R_1$s are hydrogen and some are methyl groups.

7. A multiblock copolymer having the following general formula:

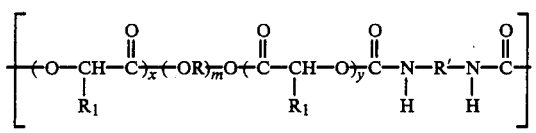

wherein R represents an alkylene group, $R_1$ is hydrogen or methyl groups and R' is hexamethylene, 4,4'-diphenylmethane, toluene, naphtalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethyl-hexamethylene and p-phenylene, or diisocyanate-terminated polyalkylene glycol chains comprising a central polyalkylene glycol chain capped by two diisocyanate compounds of the above, x and y are identical or different positive integers and m is a positive integer.

8. A multiblock copolymer as claimed in claim 7, where R is ethylene and the diisocyanate is hexamethylene diisocyanate (HDI), the polymer being of the formula

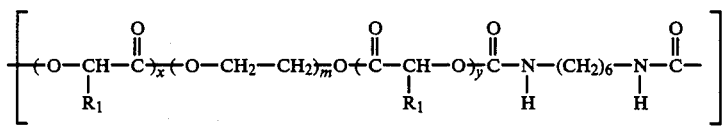

wherein $R_1$, x, y and m are as defined.

9. A multiblock copolymer as claimed in claim 7, where the dissocyanate is 4,4'-diphenylmethane diisocyanate (MDI), the polymer being of the formula

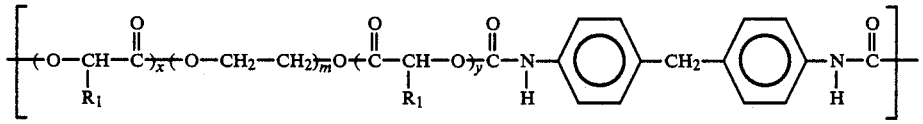

10. A multiblock copolymer according to claim 1, wherein said copolymer is in the form of at least one filament.

11. A surgical article selected from the group consisting of a suture, ligature, needle and suture combination, surgical clip, surgical staple, surgical prosthesis, textile structure, coupling, tube, support, screw or pin, where at least one of the components of each of said articles is a polymer as claimed in claim 1.

12. A compound vascular prosthesis in which a non-biodegradable graft is coated with a polymer or polymers as claimed in claim 1, the prosthesis being blood tight at implantation, and becoming, in time, sufficiently porous to facilitate tissue ingrowth and biological healing.

13. A compound vascular prosthesis as claimed in claim 12, where a knitted Dacron graft is coated with a multiblock copolymer as claimed in claim 1.

14. A substantially biodegradable vascular prosthesis comprising non-absorbable polymers and polymers as claimed in claim 1.

15. A substantially biodegradable vascular prosthesis comprising a non absorbable component selected from polyethylene terephthalate and/or polyether urethanes and/or polyether esters and/or polydimethyl siloxane polymers or copolymers, and polymers as claimed in claim 1 as the absorbable component.

16. A totally biodegradable vascular prosthesis manufactured by textile and non-textile techniques, comprising polymers as claimed in claim 1.

17. A partially biodegradable wound or burn covering comprising non absorbable polymers and polymers as claimed in claim 1.

18. A biodegradable wound or burn dressing, comprising polymers as claimed in claim 1.

19. A process of producing a multiblock copolymer having a general repeating unit I

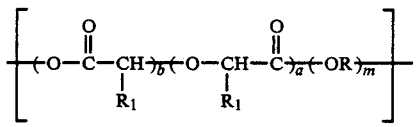

wherein R is an alkylene group, $R_1$ is hydrogen or methyl groups, m is a positive integer, and a and b are zero or positive integers, the case where a and b are simultaneously zero being excluded, produced by adding monomeric α-hydroxy carboxylic acids of the formula

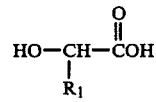

to hydroxyl-ended poly(alkylene glycol) chains, the polycondensation reaction taking place in the presence of an esterification promoting catalyst at a temperature of about 120° to 160° C., subsequently raising the temperature to about 200° C. for about 16 hours, with constant flow of dry nitrogen and then lowering the temperature to about 135° C. while a 5 mm Hg vacuum is applied for about 4 hours.

20. A process according to claim 19 wherein said catalyst is $Sb_2O_3$.

21. A process for chain extending triblock copolymers of formula IV

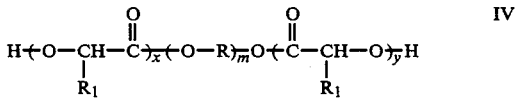

wherein R, X, y and m are as defined, said triblock polymers, which are produced by the polycondensation reaction of monomeric α-hydroxy carboxylic acid, having the formula

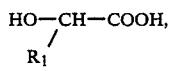

in the presence of hydroxyl-terminated poly(alkylene glycol) chains, are extended by adding to the polymers produced thereby, a diisocyanate chain extension agent of general formula OCN—R′—NCO, wherein R′ is hexamethylene, 4,4′-diphenylmethane, toluene, naphtalene, 4,4′-dicyclohexylmethane, cyclohexyl, 3,3′-dimethylphenyl, 3,3′-dimethyl-diphenylmethane, 4,6′-xylylene, 3,5,5-trimethylcyclohexyl, 2,2,4-trimethyl-hexamethylene and p-phenylene, or diisocyanate-terminated polyalkylene glycol chains comprising a central polyalkylene glycol chain capped by two diisocyanate compounds of the above, x and y are identical or different positive integers and m is a positive integer.

22. A process as claimed in claim 21, where R is ethylene, $R_1$ is methyl and R″ is hexamethylene.

23. A multiblock copolymer having the following general formula III

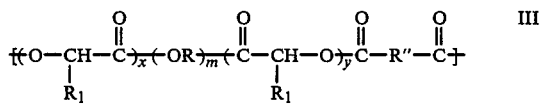

wherein R represents an alkylene group, $R_1$ is hydrogen or methyl groups, R″ is an alkylene saturated or unsaturated group or an aromatic ring, x and y are identical or different positive integers, and m is a positive integer.

24. A multiblock copolymer as claimed in claim 23, where R is ethylene, $R_1$ is methyl and R″ is ethylene.

25. A multiblock copolymer as claimed in claim 24, where R″ is an unsaturated CH=CH group.

26. A process for chain extending the triblock copolymers presented in claim 23, by adding to them carboxylic acids and derivatives as chain extention agents, the multiblock copolymers produced thereby having the following formula III

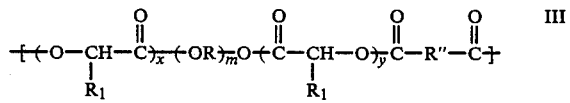

wherein R represents an alkylene group, $R_1$ is hydrogen or methyl groups, R″ is an alkylene saturated or unsaturated group or an aromatic ring, x and y are identical or different positive integers, and m is a positive integer.

27. A surgical article selected from the group consisting of a suture, ligature, needle and suture combination, surgical clip, surgical staple, surgical prosthesis, textile structure, coupling, tube, support, screw or pin, where at least one of the components of each of said articles is a polymer as claimed in claim 7.

28. A compound vascular prosthesis in which a non-biodegradable graft is coated with a polymer or polymers as claimed in claim 7, the prosthesis being blood tight at implantation, and becoming, in time, sufficiently porous to facilitate tissue ingrowth and biological healing.

29. A compound vascular prosthesis as claimed in claim 28, where a knitted Dacron graft is coated with a multiblock copolymer as claimed in claim 7.

30. A substantially biodegradable vascular prosthesis comprising non-absorbable polymers and polymers as claimed in claim 7.

31. A substantially biodegradable vascular prosthesis comprising a non-absorbable component selected from polyethylene terephthalate and/or polyether urethanes and/or polyether esters and/or polydimethyl siloxane polymers or copolymers, and polymers as claimed in claim 7 as the absorbable components.

32. A totally biodegradable vascular prosthesis manufactured by textile and non-textile techniques, comprising polymers as claimed in claim 7.

33. A surgical article selected from the group consisting of a suture, ligature, needle and suture combination surgical clip, surgical staple, surgical prosthesis, textile structure, coupling, tube support, screw or pin, where at least one of the components of each of said articles is a polymer as claimed in claim 23.

34. A compound vascular prosthesis in which a non-biodegradable graft is coated with a polymer or polymers as claimed in claim 23, the prosthesis being blood tight at implantation, and becoming, in time, sufficiently porous to facilitate tissue ingrowth and biological healing.

35. A compund vascular prosthesis as claimed in claim 34, where a knitted Dacron graft is coated with a multiblock copolymer as claimed in claim 23.

36. A substantially biodegradable vascular prosthesis comprising non-absorbable polymers and polymers as claimed in claim 23.

37. A substantially biodegradable vascular prosthesis comprising a non-absorbable component selected from polyethylene terephthalate and/or polyether urethanes and/or polyether esters and/or Polydimethyl siloxane polymers or copolymers, and polymers as claimed in claim 23 as the absorbable components.

38. A totally biodegradable vascular prosthesis manufactured by textile and non textile techniques, comprising polymers as claimed in claim 23.

39. A partially biodegradable wound or burn covering comprising non-absorbable polymers and polymers as claimed in claim 7.

40. A biodegradable wound or burn dressing comprising polymers as claimed in claim 7.

41. A partially biodegradable wound or burn dressing comprising non-absorbable polymers and polymers as claimed in claim 23.

42. A biodegradable wound or burn dressing comprising polymers as claimed in claim 23.

43. A pharmaceutical composition comprising a self-supporting film, hollow tube, beads or gel, manufactured from a multiblock copolymer as claimed in claim 1 and containing a uniformly dispersed drug contained therein.

* * * * *